(12) United States Patent
Ziegler et al.

(10) Patent No.: US 7,623,616 B2
(45) Date of Patent: Nov. 24, 2009

(54) COMPUTER TOMOGRAPHY APPARATUS AND METHOD FOR EXAMINING AN OBJECT OF INTEREST

(75) Inventors: Andy Ziegler, Hamburg (DE); Thomas Koehler, Norderstedt (DE); Michael Grass, Buchholz in der Nordheide (DE)

(73) Assignee: Kkoninklijke Philips Electronics N.V., Eindhoven (NL)

( * ) Notice: Subject to any disclaimer, the term of this patent is extended or adjusted under 35 U.S.C. 154(b) by 72 days.

(21) Appl. No.: 11/718,724

(22) PCT Filed: Nov. 2, 2005

(86) PCT No.: PCT/IB2005/053569

§ 371 (c)(1),
(2), (4) Date: May 7, 2007

(87) PCT Pub. No.: WO2006/051445

PCT Pub. Date: May 18, 2006

(65) Prior Publication Data

US 2008/0095305 A1    Apr. 24, 2008

(30) Foreign Application Priority Data

Nov. 13, 2004    (GB)    .................... 0425112.0

(51) Int. Cl.
*G01N 23/087* (2006.01)
*G01N 23/201* (2006.01)
(52) U.S. Cl. ................... 378/6; 378/5; 378/86
(58) Field of Classification Search .............. 378/4–6, 378/19, 86–89
See application file for complete search history.

(56) References Cited

U.S. PATENT DOCUMENTS

| 4,754,469 | A  | * | 6/1988  | Harding et al. | ............... 378/88 |
| 5,265,144 | A  |   | 11/1993 | Harding et al. | |
| 6,507,633 | B1 |   | 1/2003  | Elbakri et al. | |
| 6,754,298 | B2 | * | 6/2004  | Fessler | ........................ 378/4 |
| 6,950,493 | B2 | * | 9/2005  | Besson | ....................... 378/16 |
| 7,092,482 | B2 | * | 8/2006  | Besson | ....................... 378/37 |
| 2002/0150202 | A1 | | 10/2002 | Harding et al. | |
| 2003/0156684 | A1 | | 8/2003  | Fessler | |

FOREIGN PATENT DOCUMENTS

EP    1062914 A1    12/2000
JP    10206547      7/1998

(Continued)

OTHER PUBLICATIONS

U. Van Stevendall et al , "A Reconstruction Algorithm for Coherent Scatter Computed Tomography Based on Filtered Back-Projection", Med. Phys. 30(9), p. 2465-2474, 2003.

(Continued)

*Primary Examiner*—Edward J Glick
*Assistant Examiner*—Thomas R Artman

(57) ABSTRACT

A computer tomography apparatus (100) for examination of an object of interest (107), the computer tomography apparatus (100) comprising detecting elements (123) adapted to detect electromagnetic radiation coherently scattered from an object of interest (107) in an energy-resolving manner, and a determination unit (118) adapted to determine structural information concerning the object of interest (107) based on a statistical analysis of detecting signals received from the detecting elements (123).

19 Claims, 3 Drawing Sheets

FOREIGN PATENT DOCUMENTS

| | | |
|---|---|---|
| JP | 11218486 | 10/1999 |
| WO | 2004002316 A1 | 1/2004 |
| WO | 2004066215 A1 | 8/2004 |

OTHER PUBLICATIONS

I.D.Jupp et al, "The Non-Invasive Inspection of Baggage Using Coherent X-Ray Scattering", IEEE Transactions on Nuclear Science, IEEE Service Center, New York, NY, vol. 47, No. 6, pp. 1987-1994, Dec. 2000.

Lucas Parra et al, "List-Mode Likelihood: EM Algorithm and Image Quality Estimation Demonstrated on 2-D Pet", IEEE Trans. Med. Img., vol. 17, No. 2, p. 228-235, 1998.

M. Sonka et al, Handbook of Medical Imaging, Vol. 2, Pagesa 1-70, 2000.

\* cited by examiner

COMPUTER TOMOGRAPHY APPARATUS AND METHOD FOR EXAMINING AN OBJECT OF INTEREST

The invention relates to the field of X-ray imaging. In particular, the invention relates to a computer tomography apparatus, to a method of examining an object of interest with a computer tomography apparatus, to a computer-readable medium and to a program element.

Over the past several years, X-ray baggage inspections have evolved from simple X-ray imaging systems that were completely dependent on an interaction by an operator, to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector.

Computed tomography (CT) is a process of using digital processing to generate a three-dimensional image of the internals of an object from a series of two-dimensional X-ray images taken around a single axis of rotation. The reconstruction of CT images can be done by applying appropriate algorithms.

An imaging technique based on coherently scattered X-ray photons or quanta is the so-called "coherent scatter computer tomography" (CSCT). CSCT is a technique that produces images of (particularly the low angle) scatter properties of an object of interest. These depend on the molecular structure of the object, making it possible to produce material-specific maps of each component. The dominant component of low angle scatter is coherent scatter. Since coherent scatter spectra depend on the atomic arrangement of the scattering sample, coherent scatter computer tomography (CSCT) is a sensitive technique for imaging spatial variations in the molecular structure of baggage or of biological tissue across a two-dimensional object section.

It would be desirable to have a highly efficient image reconstruction scheme.

The invention provides a computer tomography apparatus, a method of examining an object of interest with a computer tomography apparatus, a computer-readable medium and a program element with the features according to the independent claims.

According to the invention, a computer tomography apparatus for examination of an object of interest comprises detecting elements adapted to detect X-rays coherently scattered from an object of interest in an energy-resolving manner, and a determination unit adapted to determine structural information concerning the object of interest based on a statistical analysis of detecting signals received from the detecting elements.

Further, the invention provides a method of examining an object of interest with a computer tomography apparatus, the method comprising the steps of detecting X-rays coherently scattered from an object of interest in an energy-resolving manner, and determining structural information concerning the object of interest based on a statistical analysis of the detected signals.

Moreover, the invention provides a computer-readable medium, in which a computer program for examining an object of interest with a computer tomography apparatus is stored which, when being executed by a processor, is adapted to carry out the above-mentioned method steps.

Beyond this, a program element for examining an object of interest is provided, which, when being executed by a processor, is adapted to carry out the above-mentioned method steps.

The examination of an object of interest according to the invention can be realized by a computer program, i.e. by software, or by using one or more special electronic optimization circuits, i.e. in hardware, or in hybrid form, i.e. by means of software components and hardware components.

The characterizing features of the invention particularly have the advantage that the reconstruction of a three-dimensional image from energy-resolving detecting signals is carried out using a statistical—in contrast to a purely deterministic—analysis of detecting signals received from a plurality of detecting elements. Thus, the reconstruction scheme of the invention takes into account the photons statistics and preferably allows the reconstruction using both the position and the energy information of each photon individually. With energy-resolving detectors being implemented in the CSCT system of the invention, the information of each photon can be used to reach the highest image quality possible. Thus, the invention introduces a statistical evaluation model of coherent scatter computed tomography so that probability distributions may be calculated, and it may be determined on the basis of a previously carried out statistical analysis which three-dimensional image of an object of interest is indeed present with a high or the highest probability. Thus, in contrast to a purely deterministic model, the invention considers stochastic information derived from an energy-resolving statistical analysis of coherently scattered electromagnetic radiation, particularly X-rays.

A statistical model which is preferably used for the statistical analysis of the invention is the so-called Maximum Likelihood model. A statistical analysis on the basis of "Maximum Likelihood" involves a reconstruction algorithm with significant advantages concerning sensitivity. Preferably on the basis of a derived Log-Likelihood function for CSCT, the energy information and the position information of each individual photon can be considered individually. Further, energy-dependent attenuation maps can be introduced in the analysis, as well as any trajectory and any detector shape. The invention provides a Maximum Likelihood function which takes into account the contribution of each individual photon, thus improving the signal-noise-ratio.

By using a high amount of available information, namely the information of each of the scattered photons individually, maximum information may be derived from a measurement, and thus the accuracy of a computer tomography analysis is significantly increased.

A Log-Likelihood function for CSCT is provided by the invention which can be maximized by a derived iterative update step. The Log-Likelihood function takes care of the photons statistics and takes into account the information of each photon separately. In addition, the method of the invention is valid for any trajectory, detector shape, beam geometry (e.g. fan-beam, cone-beam, etc.), and it supports an energy-dependent attenuation map.

Since the Log-Likelihood is valid for each q-plane individually, an independent calculation for each q-plane is possible, which facilitates parallel processing.

In statistics, "Maximum Likelihood" is a method of point estimation that uses as an estimate of an unobservable population parameter the member of the parameter space that maximizes the likelihood function. The variable h denotes an observable population parameter to be estimated. X denotes a random variable observed. The probability of an observed outcome X=x (or the value at x of the probability density function of the random variable X as a function of h with x held fixed) is the likelihood function $L_{X=x}(h)$:

$$L_{X=x}(h)=P(X=x|h) \quad (1)$$

The value of h that maximizes L(h) is the Maximum Likelihood estimate of h. Taking the logarithm of the Likelihood yields a so-called Log-Likelihood term.

The invention provides a Log-Likelihood function taking care of the photon statistics and taking into account the information of each photon individually. In addition, it is valid for any trajectory and any beam geometry (e.g. fan-beam, cone-beam). Since the Log-Likelihood is valid for each q-plane individually, an independent calculation for each q-plane is possible, which facilitates parallel processing. This further increases the speed of reconstruction compared to a global Log-Likelihood maximation. In addition, the Log-Likelihood supports an energy-dependent attenuation map.

The invention can be applied advantageously in coherent scatter computed tomography (CSCT) for single-sliced detectors and for multi-sliced detectors, particularly where at least a part of the detector is energy-resolved.

Thus, the invention is related to CSCT/CT devices in which images are reconstructed by taken into account measurements of at least some individual photons statistics (position and energy) and wherein images are reconstructed using the measurements and a Maximum Likelihood model.

According to the invention, any energy value of a photon can be taken into account and can be measured by the detecting elements. Thus, the invention may—but is not restricted to—use only two different values of energy, but may allow at least three different values of energy, or may allow a continuous (or quasi-continuous) energy spectrum of the detected photons.

Referring to the dependent claims, further preferred embodiments of the invention will be described in the following.

Next, preferred embodiments of the computer tomography apparatus of the invention will be described. These embodiments may also be applied for the method of examining an object of interest with a computer tomography apparatus, for the computer-readable medium and for the program element.

In the computer tomography apparatus, the determination unit may be adapted to determine structural information concerning the object of interest based on an analysis of a position and an energy of detecting signals. By taking into account—in the frame of a statistical analysis model—both the position of a detection signal at an array detector formed by the plurality of detecting elements, and the energy of the detected signals, by implementing an energy-resolving detecting element, all of the information available can be used to reconstruct the three-dimensional image of the object of interest.

Further, the determination unit may be adapted to determine structural information concerning the object of interest based on an analysis of detecting signals of each quantum of electromagnetic radiation individually. An individual consideration of each photon detected at the detecting elements allows to increase the reliability of the results of the statistical model of the invention.

The determination unit may be adapted to determine structural information concerning the object of interest based on a Maximum Likelihood analysis of detecting signals. Although any alternative statistical model can be applied to the computer tomography apparatus of the invention, the preferred statistical model to be implemented is Maximum Likelihood, since this architecture is particularly appropriate for using the energy and position information of each individual photon, thus increasing the efficiency and the accuracy of the reconstructed image of the object of interest.

The determination unit may be adapted to determine structural information concerning the object of interest based on a Log-Likelihood analysis of detecting signals, i.e. by analyzing the logarithm of a Maximum Likelihood function.

The determination unit may be adapted to determine structural information concerning the object of interest under consideration of experimentally and/or theoretically predetermined or preknown values of an absorption coefficient. An experimental estimation of the absorption coefficient can include performing a transmission tomography reference scan. Reliable values for absorption coefficients can also be derived from a well justified approximation (see, for instance, van Stevendaal, U. et al. "A reconstruction algorithm for coherent scatter computed tomography based on filtered back-projection", Med. Phys. 30(9), 2003).

The determination unit may be adapted to determine structural information concerning the object of interest under consideration of energy-dependent attenuation maps. By taking into account the energy-dependence of the attenuation of electromagnetic radiation traversing the object of interest, the reliability of the results of the analysis of the invention is increased.

The determination unit of the computer tomography apparatus may be adapted to determine structural information concerning the object of interest under consideration of an energy-dependence of an acceptance of the detecting elements. Considering the acceptance or geometrical sensitivity to measure a particular photon coming from a particular voxel (the three-dimensional analogue of a pixel) of an object of interest, allows to reconstruct the image of the object of interest with high accuracy, since it refines the used model.

Moreover, the determination unit may be adapted to determine structural information concerning the object of interest based on an iterative analysis of detecting signals. Such an iterative procedure—particularly in combination with the Maximum Likelihood method—is a straight forward scheme to obtain the desired information.

The determination unit may be further adapted to determine structural information concerning an object of interest based on an analysis of detecting signals which is carried out individually for different values of a momentum transfer, particularly for each plane of momentum transfers q. Such a momentum transfer from a photon to a scatter centre (e.g. an atom) may occur during a scatter process. Particularly, a Log-Likelihood model is valid for each q-plane individually, so that an independent calculation for each q-plane is possible to facilitate parallel processing.

The detecting elements of the computer tomography apparatus may be adapted to detect a predetermined number of quanta of electromagnetic radiation or to detect quanta of electromagnetic radiation for a predetermined time interval. By restricting the analysis to either a given number of photons to be detected or alternatively to a given radiation time, results from the analysis of different measurements/scans are better comparable so that highly reproducible and meaningful results can be obtained.

The computer tomography apparatus of the invention may be adapted as a coherent scatter computed tomography apparatus (CSCT), i.e. the computer tomography apparatus may be configured and operated according to the CSCT technology described above.

The computer tomography apparatus may further comprise an electromagnetic radiation source adapted to emit electromagnetic radiation to an object of interest, and may comprise a collimator arranged between the electromagnetic radiation source and the detecting elements, the collimator being adapted to collimate an electromagnetic radiation beam emitted by the electromagnetic radiation source to form a fan-beam, a cone-beam, or a beam of any other desired geometry. Alternatively to a fan-beam configuration, a cone-beam configuration can be used.

The detecting elements of the computer tomography apparatus may form a single-slice detector array, or alternatively a multi-slice detector array. A single-slice detector array has the advantage of a simple configuration and a fast evaluation of the detected signals. However, a multi-slice detector array may be implemented to achieve a particularly high resolution of the detected signals, and a high amount of detected signals.

The computer tomography apparatus according to the invention may be configured as one of the group consisting of a baggage inspection apparatus, a medical application apparatus, a material testing apparatus and a material science analysis apparatus. A preferred field of application of the invention is baggage inspection, since the defined functionality of the invention allows a secure and reliable analysis of the content of a baggage item allowing to detect suspicious content, even allowing to determine the type of material inside such a baggage item. The invention creates a high quality automatic system that can automatically recognize certain types of material and, if desired, trigger an alarm in the presence of dangerous material. Such an inspection system may have employed the computer tomography apparatus of the invention with an X-ray radiation source for emitting X-rays which are transmitted through or scattered from the examined package to a detector allowing to detect coherently scattered radiation in an energy-resolved manner.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustration in the drawings is schematically. In different drawings, similar or identical elements are provided with the same reference signs.

Figure 1:
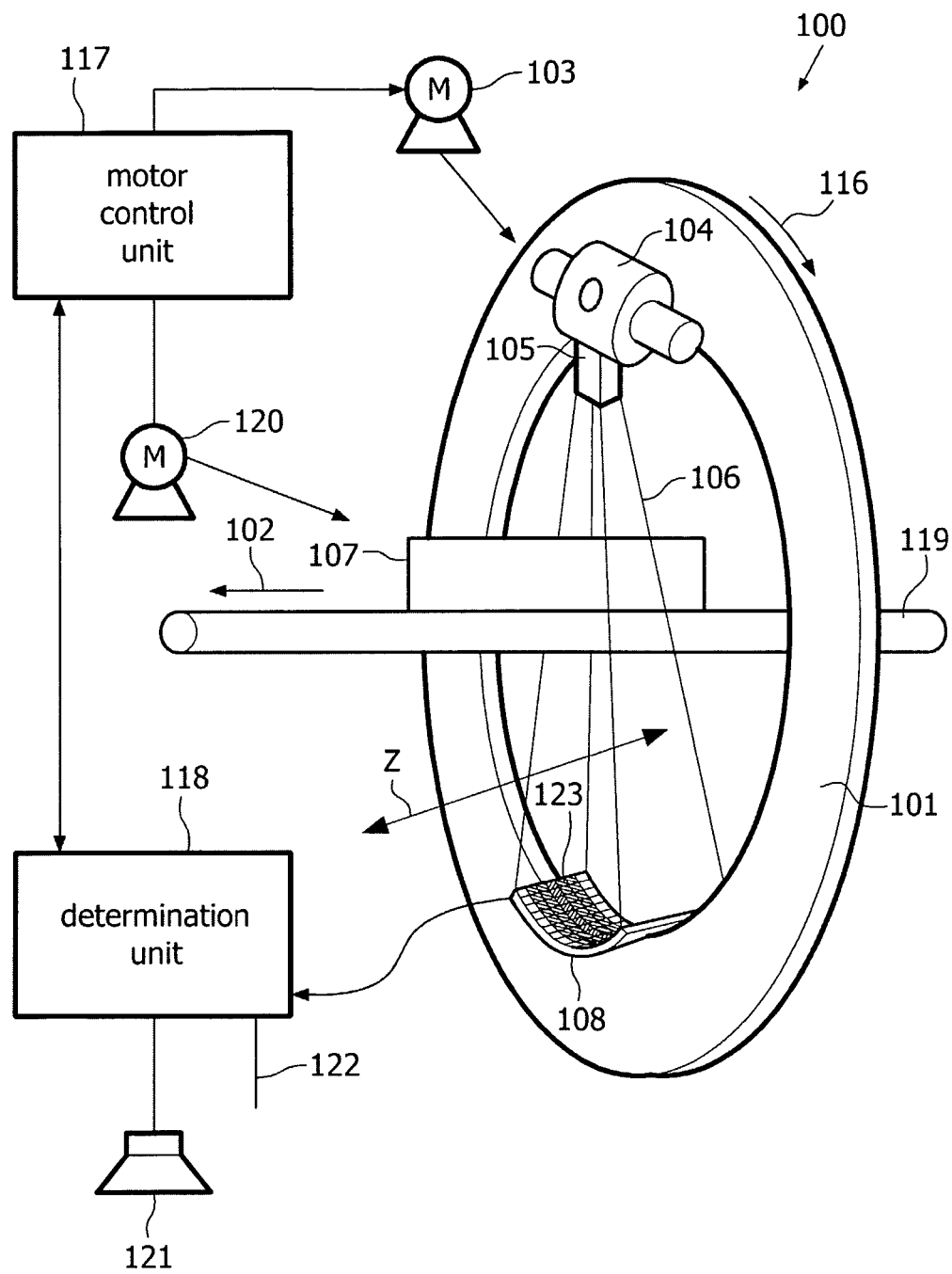
FIG. 1 shows a computer tomography apparatus according to an exemplary embodiment of the invention.

FIG. 1 shows an exemplary embodiment of a CSCT (coherent scatter computed tomography) scanner system according to the present invention. With reference to this exemplary embodiment, the present invention will be described for the application in baggage inspection to detect hazardous materials, such as explosives, in items of baggage. However, it should be noted that the present invention is not limited to this application, but may also be applied in the field of medical imaging, or other industrial applications such as material testing.

The computer tomography apparatus 100 depicted in FIG. 1 is a cone-beam CT scanner. However, the invention may also be carried out with a fan-beam geometry. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits a polychromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CSCT scanner, and impinges onto the detector 108. As may be taken from FIG. 1, the detector 108 is arranged on the gantry 101 opposite to the source of radiation 104, such that the surface of the detector 108 is covered by the cone beam 106. The detector 108 depicted in FIG. 1 comprises a plurality of detector elements 123 each capable of detecting, in an energy-resolving manner, X-rays which have been coherently scattered by the object of interest 107.

During a scan of the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 is an item of baggage which is disposed on a conveyor belt 119. During the scan of the object of interest 107, while the gantry 101 rotates around the item of baggage 107, the conveyor belt 119 displaces the object of interest 107 along a direction parallel to the rotational axis 102 of the gantry 101. By this, the object of interest 107 is scanned along a helical scan path. The conveyor belt 119 may also be stopped during the scans to thereby measure signal slices. Instead of providing a conveyor belt 119, for example in medical applications where the object of interest 107 is a patient, a moveable table is used. However, it should be noted that in all of the described cases it is also possible to perform a circular scan, where there is no displacement in a direction parallel to the rotational axis 102, but only the rotation of the gantry 101 around the rotational axis 102.

Further, it shall be emphasized that, as an alternative to the cone-beam configuration shown in FIG. 1, the invention can be realized by a fan-beam configuration. In order to generate a primary fan-beam, the aperture system 105 can be configured as a slit collimator.

The detector 108 is connected to the determination unit 118. The determination unit 118 receives the detection result, i.e. the read-outs from the detector elements 123 of the detector 108 and determines a scanning result on the basis of these read-outs. Furthermore, the determination unit 118 communicates with the motor control unit 117 in order to coordinate the movement of the gantry 101 with motors 103 and 120 with the conveyor belt 119.

The determination unit 118 may be adapted for reconstructing an image from read-outs of the detector 108 using a statistical method. A reconstructed image generated by the calculation unit 118 may be output to a display (not shown in FIG. 1) via an interface 122.

The determination unit 118 may be realized by a data processor to process read-outs from the detector elements 123 of the detector 108.

Furthermore, as may be taken from FIG. 1, the determination unit 118 may be connected to a loudspeaker 121, for example to automatically output an alarm in case of the detection of suspicious material in the item of baggage 107.

The computer tomography apparatus 100 for examination of the object of interest 107 includes the detector 108 having the plurality of detecting elements 123 arranged in a matrixlike manner, each being adapted to detect X-rays coherently scattered from the object of interest 107 in an energy-resolving manner. Further, the computer tomography apparatus 100 comprises the determination unit 118 adapted to determine structural information concerning the object of interest 107 based on a statistical analysis of detecting signals received from the detecting elements 123. Particularly, the determination unit 118 determines structural information concerning the object of interest 107 based on an analysis of a position and an energy of detecting signals on the detector array 108. This analysis is preferably carried out individually for each photon of electromagnetic radiation generated by the X-ray source 104 and scattered coherently onto the object of interest 107. As will be described in the following in more detail, the determination unit 118 determines structural information concerning the object of interest 107 based on a Maximum Likelihood analysis of the detecting signals. In the frame of this evaluation, structural information concerning the object of interest 107 is determined by the determination unit 118 under consideration of experimentally preknown values of an absorption coefficient. The determination unit 118 takes into account, for determining structural information concerning the object of interest 107, energy-dependent attenuation maps. Further, the structural information are reconstructed considering an energy-dependence of an acceptance of the detecting elements 123. The analysis carried out by the determining unit 118 includes an iteration.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. Alternatively, not shown in FIG. 1, a slit collimator can be used instead of collimator 105 to produce a fan-beam. The detecting elements 123 form a multi-slice detector array 108. The computer tomography apparatus 100 is configured as a baggage inspection apparatus.

In the following, referring to FIG. 2 and FIG. 3, the statistic analysis carried out by the determination unit 118 will be described in more detail.

Figure 2:
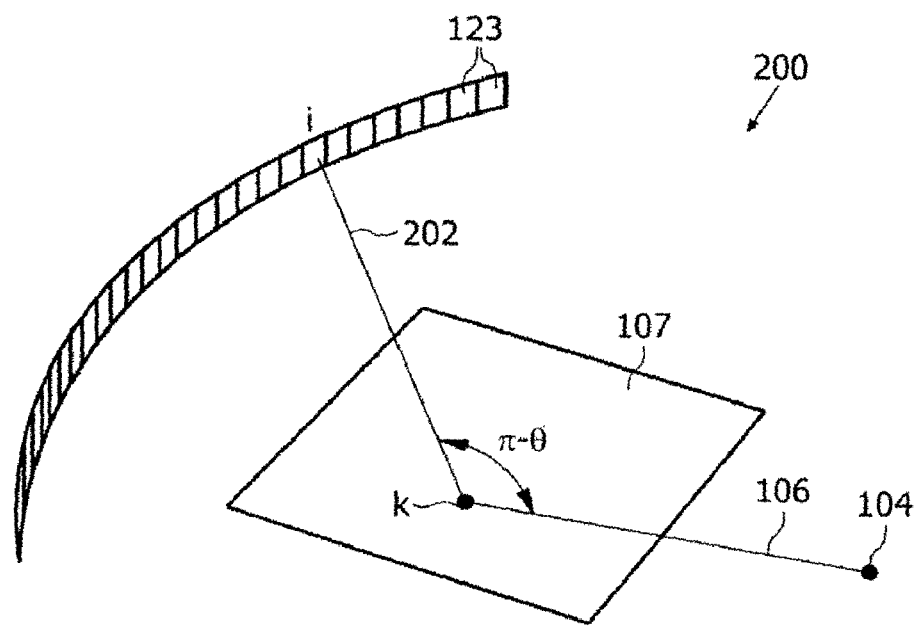
FIG. 2 and FIG. 3 show schematic views of a computer tomography apparatus according to the invention based on which an exemplary embodiment of the statistical analysis of the invention is explained.

Referring to FIG. 2, a scheme 200 will be explained which illustrates a scratch of the geometry of coherent scatter CT and a possible flight path of a photon. The scheme 200 shows the X-ray source 104 emitting a primary beam 106 which is scattered at an voxel k of the object of interest 107, wherein, the scatter angle is defined by an angle $\Theta$. A coherently scattered beam 202 impinges one of the detecting elements 123 to generate an energy-resolved detecting signal at this particular detecting element. In other words, a photon is emitted at the X-ray source 104, is scattered at the voxel k under a certain angle $\Theta$, and the energy $E_i$ of the photon is measured in the detector pixel i.

In the following, the derivation of an exact individual photon based Maximum Likelihood function will be described, based on the geometric scheme illustrated in FIG. 2.

A photon or quantum i is measured in a detector element 123 with a photon energy $E_i$. An aim of the following considerations is to calculate the probability density that this photon was coherently scattered at any of the K voxels j with the coordinate $x_j$. All absorption coefficients $\mu_j$ are known exactly from a well-known transmission tomography scan, or approximately from a well justified approximation, see the above-mentioned work of van Stevendaal et al.

Under the assumption that the photon has been coherently scattered at the voxel k with the coordinate $x_k$, an attenuation $A_{att,plane}^i$ from the source 104 to the voxel $x_k$ is given by $$A_{att,plane}^i(x_k) = e^{-\sum_{j=1}^{k-1} l_{ij}\mu_j} \qquad (2)$$

where $l_{ij}$ is a basis function of the voxel grid, while the attenuation $A_{att,scat}^i$ from the voxel $x_k$ to the detector element 123 can be calculated by $$A_{att,scat}^i(x_k) = e^{-\sum_{j=k}^{K} l_{ij}\mu_j} \qquad (3)$$

The total attenuation $A_{att}^i(x_k)$ of the photon i is $$A_{att}^i(x_k) = A_{att,plane}^i(x_k) * A_{att,scat}^i(x_k) \qquad (4)$$

The attenuation considers the absorption of electromagnetic radiation traversing the object of interest 107.

Since the energy of the photon is known and remains unchanged during the process of coherent scatter, energy-dependent attenuation maps can be used.

A probability density $p(E_i|x_k)$ that a photon i with energy $E_i$ reaches the detector 108 is given by $$p(E_i | x_k) = p(A_{att,k}^i) \cdot P(\theta_i(x_k)) = \frac{A_{att}^i(x_k)}{\sum_{m=1}^{K} A_{att}^i(x_m)} \cdot \frac{1+\cos^2\theta_i(x_k)}{1.5\pi} \qquad (5)$$

The function $P(\Theta_i(x_k))$ defines the probability that a photon is coherently scattered under a certain angle $\Theta_i(x_k)$ (see FIG. 2) and is given by the Thompson formula, see equation (5). The Thomson formula describes the probability that a photon is scattered under a particular angle.

A geometrical sensitivity (or acceptance) $s_{k,i}$ to measure the photon i coming from the voxel k consists of the steradian (the three-dimensional analog of an angle), which is seen from the detector element 123. For example: in fan-beam geometry with a parallel detector (see FIG. 3), this sensitivity is given by $$s_{k,i,E_i} = \frac{\Delta L_{k,i}}{2\pi R_i} \cdot a_{E_i} \qquad (6)$$

The acceptance includes the possibility that the detection of a photon is prevented, e.g. since the photon is absorbed by blades of a collimator.

Figure 3:
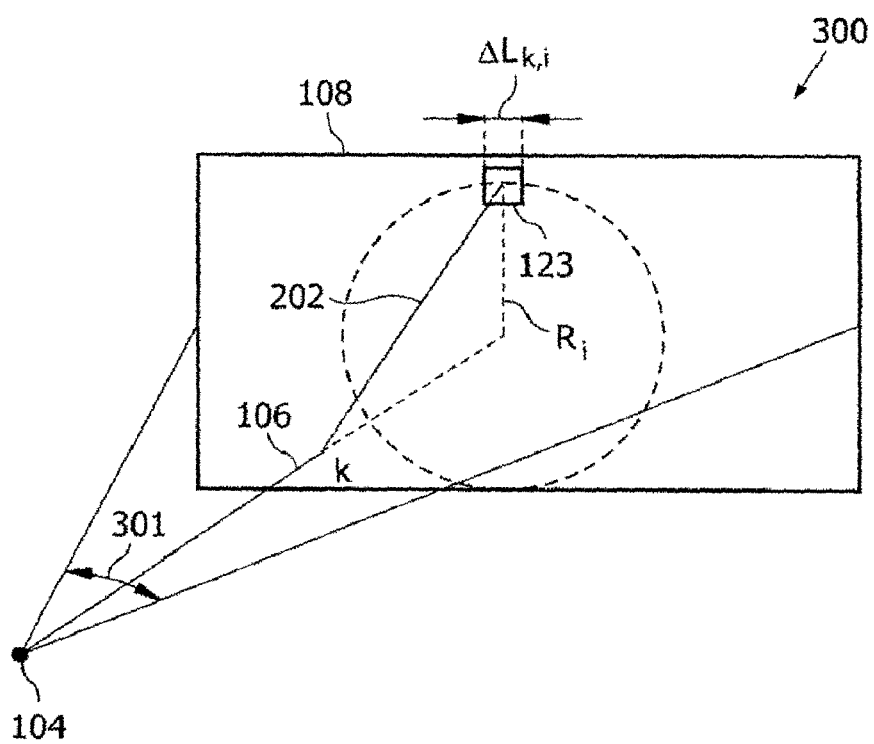

FIG. 3 shows a scheme 300 of X-ray beams 106 coming from the source 104 with primary radiation in a fan-beam configuration 301, wherein the primary X-ray beam 106 is scattered at a voxel k so that a coherently scattered beam 202 impinges a detector element 123 of the detector 108. Thus, FIG. 3 shows the geometrical sensitivity for a fan-beam 301 geometry with a parallel detector 108. A photon is coherently scattered at voxel k, and the distance between its detection in pixel i and its position without scatter (see dashed line) defines a distance $R_i$. The size and collimation of the detector pixels 123 defines a length, $\Delta L_{k,i}$, of a circle with radius $R_i$.

In equation (6), $\Delta L_{k,i}$ is the length of the circle described by the radius $R_i$, which is seen by the detector element 123, which registers the photon i. This takes into account any collimation on the detector 108. The acceptance $\alpha_E$, takes care of the energy depending acceptance of the detector pixels 123.

The probability $P(x_k|q_{r,k}(E_i,x_k))$ that a photon with an energy $E_i$ which falls in the bin r of $q_{r,k}$ for a fixed k, is scattered at voxel $x_k$ and is measured in detector i is given by $$P(x_k \mid q_{r,k}(E_i, x_k)) = \frac{q_{r,k}(E_i, x_k) s_{k,i,E_i}}{\sum_{i=1,i\in A}^{N} \sum_{m=1}^{K} q_{r,m}(E_i, x_m) s_{m,i,E_i}} \quad (7)$$

where $q(E_i, x_k) = 2 E_i \sin(\Theta_i(x_k)/2)/\hbar c$ and $A_{r,k} = \{i | q_{r,k} < q(E_i, x_k) < q_{r+1,k}\}$ with $N_{r,k}$ elements. For simplification, it is defined $\sum_{i=1}^{N_{r,k}} := \sum_{i=1, i\in A_{r,k}}^{N}$. The distribution of q with $(q_{r,1}, \ldots, q_{r,K})$ is to determined by finding a set of $q_{r,k}$ which maximizes the likelihood $$L(E_1, \ldots, E_n \mid q) = \prod_{i=1}^{N} p(E_i \mid q) \quad (8)$$

which is given by the probability density $p(E_i|q)$ for all N photons which were measured. The probability $p(E_i|q)$ is given by $$p(E_i \mid q) = \sum_{k=1}^{K} (p(E_i \mid x_k) \cdot P(x_k \mid q_{r,k}(E_i, x_k))) \quad (9)$$

$$= \sum_{k=1}^{K} \left( \frac{A_{att}^i(x_k)}{\sum_m A_{att}^i(x_m)} \cdot \frac{1 + \cos^2\theta_i(x_k)}{1.5\pi} \cdot \frac{q_{r,k}(E_i, x_k) s_{k,i,E_i}}{\sum_{i=1}^{N_r} \sum_m q_{r,m}(E_i, x_m) s_{m,i,E_i}} \right)$$

The Log-Likelihood function is $$L(E_1, \ldots, E_N \mid q) = \sum_{i=1, i\in B}^{N} \ln p(E_{i_r} \mid q) \quad (10)$$

$$= \sum_{i=1}^{N_r} \ln\left(\sum_{k=1}^{K} p(E_i \mid x_k) q_{r,k}(E_i, x_k) s_{k,i,E_i}\right) -$$

$$N_r \ln\left(\sum_{k=1}^{K} \sum_{i=1}^{N_{r,m}} q_{r,k}(E_i, x_k) s_{k,i,E_i}\right)$$

which is to be maximized, where $B = \cup_{k=1}^{K} A_{r,k}$ with $N_r$ elements and $\sum_{i=1}^{N_r} := \sum_{i=1, i\in B}^{N}$.

The Log-Likelihood function of equation (10) can—if desired or appropriate—be extended by a penalty function $R(q)$, which could be a first-order neighbourhood and pairwise pixel difference penalty function like $$R(q) = \sum_{i=1}^{N_r} \frac{1}{2} \sum_{k \in \aleph_j} \Psi(q_j - q_k) \quad (10a)$$

where $N_j$ is the neighbourhood of the j-th pixel (e.g., left, right, up, down) and $\Psi$ called the potential function. Then the Log-Likelihood function reads $$L(E_1, \ldots, E_N \mid q) = \sum_{i=1, i\in B}^{N} \ln p(E_{i_r} \mid q) \quad (10b)$$

$$= \sum_{i=1}^{N_r} \ln\left(\sum_{k=1}^{K} p(E_i \mid x_k) q_{r,k}(E_i, x_k) s_{k,i,E_i}\right) -$$

$$N_r \ln\left(\sum_{k=1}^{K} \sum_{i=1}^{N_{r,m}} q_{r,k}(E_i, x_k) s_{k,i,E_i}\right) + \beta R(q)$$

where the parameter $\beta$ sets the strength of the cost function $R(q)$. For $\beta=0$, the equation (10) is recovered (for detailed information concerning the function R, see Handbook of Medical Imaging, Volume 2, pp. 1-70, 2000, Eds.: M. Sonka, J. M. Fitzpatrick).

During the measurement, the measurement time T can be fixed and the total count N becomes an additional random variable measured during the experiment, which may be denoted as "present-time". Alternatively, the total numbers of counts N can be fixed, in which case the measurement time T becomes a stochastic variable (denoted as "present-count"). In the "present-time" case, the Log-Likelihood function changes to $$L(E_1, \ldots, E_N \mid q) = \sum_{i=1}^{N_r} \ln p(E_{i_r} \mid q) + P(N \mid T, q) + \beta R(q) \quad (11)$$

and in the "present-count" case to $$L(E_1, \ldots, E_N \mid q) = \sum_{i=1}^{N_r} \ln p(E_{i_r} \mid q) + P(T \mid N, q) + \beta R(q) \quad (12)$$

where $P(N|T,q)$ and $P(T|N,q)$ describe the probabilities for "present-time" and "present-count", respectively.

In the following, a possible iterative solution of the presented Log-Likelihood function will be described.

The derivation of the iterative solution without the cost function $R(q)$ (i.e. for the case $\beta=0$) is leaned against a similar derivation for PET ("Positron Emission Tomography") reconstruction, see Parra, L, Barett, H H "List-Mode Likelihood: EM Algorithm and Image Quality Estimation Demonstrated on 2-D PET", IEEE Trans. Med. Img., volume 17, no. 2, pages 228-235, 1998.

Equation (9) may be regarded as a density mixture model, where the $p(E_i|x_k)$ corresponds to densities of the mixture model and $P(x_k|q(x_k,E_i))$ to the mixture coefficients. For the mixture model, the data are extended by the unobserved variables $z_{rk,i}$ (see Dempster, A, Laird, N and Rubin, D "Maximum likelihood from incomplete data via the EM algorithm", J. Roy. Stat. Soc. volume B 39, pages 1-38, 1977). The unobserved variables $z_{rk,i}$ are defined for each bin r by $$z_{rk,i} \equiv \begin{cases} 1, & \text{if event } i \text{ originated in bin } r, k \\ 0, & \text{otherwise} \end{cases} \quad (13)$$

The column vector $z_{rk}$ contains only one nonzero entry. The $z_{rk}$ are independently drawn from the $P(x_{z_{rj}}|q) = \Sigma_k z_{rk,i} P(x_k|q)$.

The Log-Likelihood of the complete data for "present-count" is $(E_1, Z_{r1}, \ldots, E_N, z_{rN}, T)$, and the likelihood function can be written as $$L(E_1, z_r, \ldots, E_N, z_{rN}, T | N, q) = \sum_{i=1}^{N_r} \ln p(E_i, x_{z_{r,i}} | q) + \ln(T|N,q) \quad (14)$$

$$= \sum_{i=1}^{N_r} \ln P(x_{z_{r,i}} | q) + \sum_{i=1}^{N_r} \ln p(E_i | x_{z_{r,i}}, q) + \ln p(T|N,q)$$

$$= \sum_{i=1}^{N_r} \sum_k z_{rk,i}(\ln P(x_k|q) + \ln p(E_i|x_k)) + \ln p(T|N,q)$$

Equation (14) follows the definition of equation (13) and the mixture of equation (9). The measurement time T is the sum of $N_r$ interarrival times, and follows an Erlang density, $p(T|N_r,q)$, given by $$p(T|N_r,q) = \frac{(\lambda_r T)^{N_r}}{T} e^{-\lambda T} / (N_r - 1)! \quad (15)$$

where $\lambda_r = \sum_{i=1}^{N_r} \sum_{k=1}^{K} q_{r,k} s_{k,j,E}$, is the mean rate of the Poisson distribution.

In the E-step, the estimate of $L(\ldots|N,q)$ is computed given the actual measurement data $E_1, \ldots, E_N, T$ and fixed $q^{(t)}$, i.e., marginalize $L(\ldots|N,q)$ over the hidden variables. This can be denoted in short by $$Q(q|q^{(t)}) = E[L(E_1,z_{r1},\ldots,E_N,z_{rN},T|N,q)|(E_1,\ldots,E_N, T|N_r,q^{(t)}] \quad (16)$$

Since equation (14) is linear in $z_{rk,i}$ this amounts to replacing $z_{rk,i}$ by its expected value $\bar{z}_{rk,i}$, which is $$\bar{z}_{rk,i}(q^{(t)}) = P(x_k|E_i, q^{(t)}) = \frac{p(E_i, x_k|q^{(t)})}{p(E_i|q^{(t)})} = \frac{P(x_k|q^{(t)})p(E_i|x_k)}{\sum_{l=1}^{K} P(x_l|q^{(t)})p(E_i|x_l)} \quad (17)$$

Here, $p(E_i,x_k|q^{(t)})$ denotes a joint probability (density) for $x_k$ and $E_i$. In the M-step, the maximum of the expectation of L has to be computed, which is obtained by solving for vanishing derivates $$\frac{\partial Q(q|q^{(t)})}{\partial q_{r,l}} = \quad (18)$$

$$\frac{\partial}{\partial q_{r,l}} \sum_{i=1}^{N_r} \sum_{k=1}^{K} \bar{z}_{rk,i}(q^{(t)}) \ln \frac{q_{r,k}(E_i, x_k) s_{k,i,E_i}}{\sum_{m=1}^{K} \sum_{i=1}^{N_{r,m}} q_{r,m}(E_i, x_m) s_{m,i,E_i}} +$$

-continued $$\underbrace{\frac{\partial}{\partial q_{r,l}} \sum_{i=1}^{N_r} \sum_{k=1}^{K} z_{rk,i}(q^{(t)}) \ln \left( \frac{A_{att}^i(x_k)}{\sum_m A_{att}^i(x_m)} \frac{1+\cos^2 \theta_i(x_k)}{1.5\pi} \right)}_{=0} +$$

$$\frac{\partial}{\partial q_{r,l}} \left\{ N_r \ln \left( T \sum_{m=1}^{K} \sum_{i=1}^{N_{r,m}} q_{r,m}(E_i, x_m) s_{m,i,E_i} \right) - T \sum_{m=1}^{K} \sum_{i=1}^{N_{r,m}} q_{r,m}(E_i, x_m) s_{m,i,E_i} \right\} =$$

$$\sum_{i_r=1}^{N_r} z_{rl,i}(q^{(t)}) \frac{1}{q_{r,l}(E_i, x_k)}$$

$$\frac{\sum_{m=1}^{K} \sum_{i=1}^{N_{r,m}} q_{r,m}(E_i, x_m) s_{m,i,E_i} - q_{r,l}(E_i, x_l) s_{l,i,E_i}}{\sum_{m=1}^{K} \sum_{i=1}^{N_{r,m}} q_{r,m}(E_i, x_m) s_{m,i,E_i}} +$$

$$N_r \frac{\sum_{i=1}^{N_{r,l}} s_{l,i,E_i}}{\sum_{m=1}^{K} \sum_{i=1}^{N_{r,m}} q_{r,m}(E_i, x_m) s_{m,i,E_i}} - T \sum_{i=1}^{N_{r,l}} s_{l,i,E_i} =$$

$$\sum_{i=1}^{N_r} \frac{z_{rl,i}(q^{(t)})}{q_{r,k}(E_i, x_k)} - \frac{\left( \sum_{i=1}^{N_r} z_{rl,i}(q^{(t)}) \right) \sum_{i=1}^{N_{r,l}} s_{l,i,E_i}}{\sum_{m=1}^{K} \sum_{i=1}^{N_{r,m}} q_{r,m}(E_i, x_m) s_{m,i,E_i}} +$$

$$N_r \frac{\sum_{i=1}^{N_{r,l}} s_{l,i,E_i}}{\sum_{m=1}^{K} \sum_{i=1}^{N_{r,m}} q_{r,m}(E_i, x_m) s_{m,i,E_i}} - T \sum_{i=1}^{N_{r,l}} s_{l,i,E_i} =$$

$$\sum_{i=1}^{N_r} \frac{z_{rl,i}(q^{(t)})}{q_{r,k}(E_i, x_k)} - T \sum_{i=1}^{N_{r,l}} s_{l,i,E_i} = 0$$

This gives for the maximum $q_{r,k}^{(t+1)} = (T \sum_{i=1}^{N_{r,l}} s_{l,m,E_m})^{-1} \sum_{i=1}^{N_r} \bar{z}_{rk,i}(q^{(t)})$. Together with equations (7) and (16), one arrives at the fixed-point iteration:

$$q_{r,k}^{(n+1)} = \frac{1}{T \sum_{i=1}^{N_{r,k}} s_{k,i,E_i}} \sum_{i=1}^{N_{r,k}} \frac{q_{r,k}^{(n)} s_{k,i,E_i} A_{att,k}^{(i)} (1+\cos^2(\theta_i(x_k)))}{\sum_{m=1}^{K} q_{r,m}^{(n)} s_{m,i,E_i} A_{att,m}^{(i)} (1+\cos^2(\theta_i(x_m)))} \quad (19)$$

$$= \frac{1}{T \sum_{i=1}^{N_{r,k}} s_{k,i,E_i}} \sum_{i=1}^{N_{r,k}} \frac{q_{r,k}^{(n)} s_{k,i,E_i} A_{att,k}^{(i)} (1+\cos^2(\theta_i(x_k)))}{\sum_{m=1}^{K} q_{r,m}^{(n)} s_{m,i,E_i} A_{att,m}^{(i)} (1+\cos^2(\theta_i(x_m)))}$$

The restriction of the sum from $$\sum_{i=1}^{N_r} \text{ to } \sum_{i=1}^{N_{r,k}}$$

results from the fact that only the photons which can come from $q_{r,k}$ contribute to the sum.

Referring to equations (20), (21) a step by step calculation of the derivates in equation (19) is shown:

$$\frac{\partial}{\partial q_{r,l}} \sum_{i=1}^{N_r} \sum_{k=1}^{K} \bar{z}_{rk,i}(q^{(t)}) \ln \frac{q_{r,k}(E_i, x_k) s_{k,i,E_i}}{\sum_{m=1}^{K} \sum_{i=1}^{N_{r,m}} q_{r,m}(E_i, x_m) s_{m,i,E_i}} = \quad (20)$$

$$\sum_{i=1}^{N_r} \sum_{k=1}^{K} \bar{z}_{rk,i}(q^{(t)}) \frac{1}{\frac{q_{r,k}(E_i, x_k) s_{k,i,E_i}}{\sum_{m=1}^{K} \sum_{i_r=1}^{N_{r,m}} q_{r,m}(E_i, x_m) s_{m,i,E_i}}}$$

$$\frac{s_{k,i,E_i} \sum_{m=1}^{K} \sum_{i=1}^{N_{r,m}} q_{r,m}(E_i, x_m) s_{m,i,E_i} - q_{r,k}(E_i, x_k) s_{k,i,E_i} s_{l,i,E_i}}{\left(\sum_{m=1}^{K} \sum_{i=1}^{N_{r,m}} q_{r,m}(E_i, x_m) s_{m,i,E_i}\right)^2} =$$

$$\sum_{i=1}^{N_r} z_{rl,i}(q^{(t)}) \frac{1}{q_{r,k}(E_i, x_k)}$$

$$\frac{\sum_{m=1}^{K} \sum_{i=1}^{N_{r,m}} q_{r,m}(E_i, x_m) s_{m,i,E_i} - q_{r,l}(E_i, x_l) \sum_{i=1}^{N_{r,m}} S_{l,i,E_i}}{\sum_{m=1}^{K} \sum_{i=1}^{N_{r,m}} q_{r,m}(E_i, x_m) s_{m,i,E_i}}$$

$$\frac{\partial}{\partial q_{r,l}} \left\{ N_r \ln \left( T \sum_{m=1}^{K} \sum_{i=1}^{N_{r,m}} q_{r,m}(E_i, x_m) s_{m,i,E_i} \right) - T \sum_{m=1}^{K} \sum_{i=1}^{N_{r,m}} q_{r,m}(E_i, x_m) s_{m,i,E_i} \right\} = \quad (21)$$

$$N_r \frac{1}{T \sum_{m=1}^{K} \sum_{i=1}^{N_{r,m}} q_{r,m}(E_i, x_m) s_{m,i,E_i}} T \sum_{i=1}^{N_{r,m}} q_{r,l}(E_i, x_l) s_{l,i,E_i} -$$

$$T \sum_{i=1}^{N_{r,m}} s_{l,i,E_i} = N_r \frac{\sum_{i=1}^{N_{r,m}} S_{l,i,E_i}}{\sum_{m=1}^{K} \sum_{i=1}^{N_{r,m}} q_{r,m}(E_i, x_m) s_{m,i,E_i}} - T \sum_{i=1}^{N_{r,m}} s_{l,i,E_i}$$

Summarizing, referring to coherent scatter computer tomography (CSCT) using an energy-resolving detector, a penalized Log-Likelihood function for any geometry and trajectory for each scatter plane (q-plane, $q(E_i, x_k) = 2 E_i \sin(\Theta_i(x_k)/2)/\hbar c$), is described by equation (10b). In equations (10) and (10b), k and r are the voxel number and the bin of the q-plane, respectively.

According to the invention, the function according to equation (10) shall be maximized to find the image with the highest likelihood. A preferable iterative update step for each $q_{r,k}$ is given by equation (19).

Figure 4:
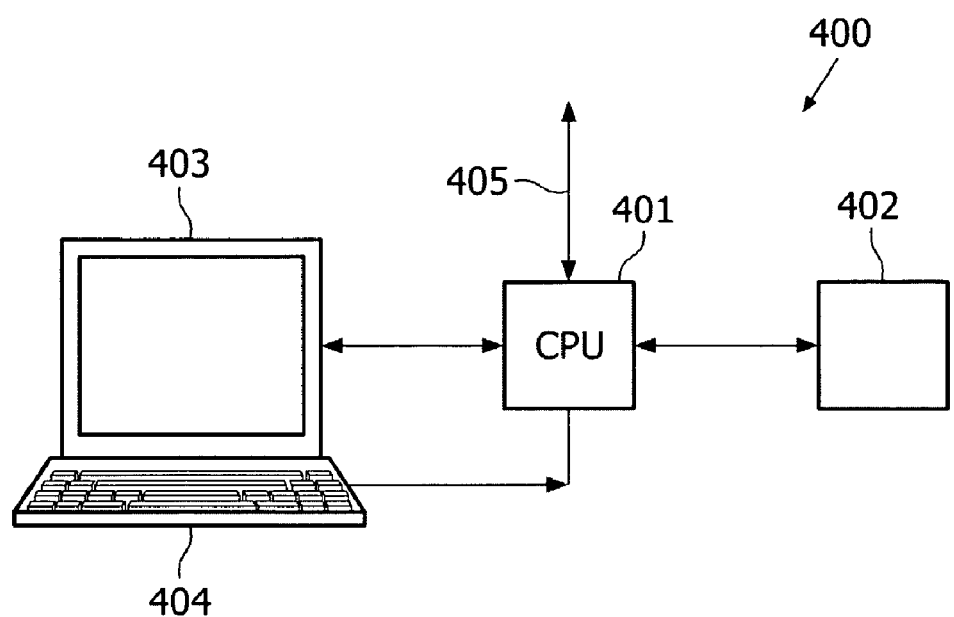
FIG. 4 shows an exemplary embodiment of a data processing device to be implemented in the computer tomography apparatus of the invention.

FIG. 4 depicts an exemplary embodiment of a data processing device 400 according to the present invention for executing an exemplary embodiment of a method in accordance with the present invention. The data processing device 400 depicted in FIG. 4 comprises a central processing unit (CPU) or image processor 401 connected to a memory 402 for storing an image depicting an object of interest, such as a patient or an item of baggage. The data processor 401 may be connected to a plurality of input/output network or diagnosis devices, such as an MR device or a CT device. The data processor 401 may furthermore be connected to a display device 403, for example a computer monitor, for displaying information or an image computed or adapted in the data processor 401. An operator or user may interact with the data processor 401 via a keyboard 404 and/or other output devices, which are not depicted in FIG. 4. Furthermore, via the bus system 405, it is also possible to connect the image processing and control processor 401 to, for example a motion monitor, which monitors a motion of the object of interest. In case, for example, a lung of a patient is imaged, the motion sensor may be an exhalation sensor. In case the heart is imaged, the motion sensor may be an electrocardiogram (ECG).

Exemplary technical fields, in which the present invention may be applied advantageously, include baggage inspection, medical applications, material testing, and material science. An improved image quality and a reduced amount of calculations in combination with a low effort may be achieved. Also, the invention can be applied in the field of heart scanning to detect heart diseases.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A computer tomography apparatus (100) for examination of an object of interest (107), the computer tomography apparatus (100) comprising:
   detecting elements (123) adapted to detect electromagnetic radiation coherently scattered from an object of interest (107) in an energy-resolving manner;
   a determination unit (118) adapted to determine structural information concerning the object of interest (107) based on a statistical analysis of position and energy information of detecting signals received from the detecting elements (123),
   wherein the statistical analysis is performed during a reconstruction process and computes a likelihood estimate that photons were coherently scattered from particular positions and angles of the object of interest (107) based on a computed probability density computed in accordance with said position and energy information of said detecting signals.

2. The computer tomography apparatus (100) according to claim 1, wherein the determination unit (118) is adapted to determine structural information concerning the object of interest (107) based on an analysis of a position and an energy of detecting signals.

3. The computer tomography apparatus (100) according to claim 1, wherein the determination unit (118) is adapted to determine structural information concerning the object of interest (107) based on an analysis of detecting signals of each quantum of electromagnetic radiation individually.

4. The computer tomography apparatus (100) according to claim 1, wherein the determination unit (118) is adapted to determine structural information concerning the object of interest (107) based on a Maximum Likelihood analysis of detecting signals.

5. The computer tomography apparatus (100) according to claim 1, wherein the determination unit (118) is adapted to determine structural information concerning the object of interest (107) based on a Log-Likelihood analysis of detecting signals.

6. The computer tomography apparatus (100) according to claim 1, wherein the determination unit (118) is adapted to determine structural information concerning the object of interest (107) under consideration of experimentally and/or theoretically predetermined values of an absorption coefficient.

7. The computer tomography apparatus (100) according to claim 1, wherein the determination unit (118) is adapted to determine structural information concerning the object of interest (107) under consideration of an energy-dependence of an attenuation of electromagnetic radiation between an electromagnetic radiation source (104) and the detecting elements (123).

8. The computer tomography apparatus (100) according to claim 1, wherein the determination unit (118) is adapted to determine structural information concerning the object of interest (107) under consideration of an energy-dependence of an acceptance of the detecting elements (123).

9. The computer tomography apparatus (100) according to claim 1, wherein the determination unit (118) is adapted to determine structural information concerning the object of interest (107) based on an iterative analysis of detecting signals.

10. The computer tomography apparatus (100) according to claim 1, wherein the determination unit (118) is adapted to determine structural information concerning the object of interest (107) based on an analysis of detecting signals which is carried out individually for different values of a momentum transfer.

11. The computer tomography apparatus (100) according to claim 1, wherein the detecting elements (123) are adapted to detect, for the statistical analysis, a predetermined number of quanta of electromagnetic radiation or to detect quanta of electromagnetic radiation for a predetermined time interval.

12. The computer tomography apparatus (100) according to claim 1, being adapted as a coherent scatter computer tomography apparatus.

13. The computer tomography apparatus (100) according to claim 1, comprising an electromagnetic radiation source (104) adapted to emit electromagnetic radiation to an object of interest (107) and comprising a collimator (105) arranged between the electromagnetic radiation source (104) and the detecting elements (123), the collimator (105) being adapted to collimate an electromagnetic radiation beam emitted by the electromagnetic radiation source (104) to form a fan-beam or a cone-beam.

14. The computer tomography apparatus (100) according to claim 1, wherein the detecting elements (123) form a single-slice detector array.

15. The computer tomography apparatus (100) according to claim 1, wherein the detecting elements (123) form a multi-slice detector array (108).

16. The computer tomography apparatus (100) according to claim 1, configured as one of the group consisting of a baggage inspection apparatus, a medical application apparatus, a material testing apparatus and a material science analysis apparatus.

17. A method of examining an object of interest (107) with a computer tomography apparatus (100), the method comprising the steps of:
  detecting electromagnetic radiation coherently scattered from an object of interest (107) in an energy-resolving manner; and
  determining structural information concerning the object of interest (107) based on a statistical analysis of the detected signals,
  wherein the statistical analysis is performed during a reconstruction process and computes a likelihood estimate that photons were coherently scattered from particular positions and angles of the object of interest (107) based on a computed probability density computed in accordance with said position and energy information of said detecting signals.

18. A computer-readable medium (402), in which a computer program of examining an object of interest (107) with a computer tomography apparatus (100) is stored which, when being executed by a processor (401), is adapted to carry out the steps of:
  detecting electromagnetic radiation coherently scattered from an object of interest (107) in an energy-resolving manner; and
  determining structural information concerning the object of interest (107) based on a statistical analysis of the detected signals;
  wherein the statistical analysis is performed during a reconstruction process and computes a likelihood estimate that photons were coherently scattered from particular positions and angles of the object of interest (107) based on a computed probability density computed in accordance with said position and energy information of said detecting signals.

19. A computer program product comprising one or more computer-readable media having thereon computer executable instructions for examining an object of interest (107) that, when executed by a processor (401), is adapted to carry out the steps of:
  detecting electromagnetic radiation coherently scattered from an object of interest (107) in an energy-resolving manner; and
  determining structural information concerning the object of interest (107) based on a statistical analysis of the detected signals;
  wherein the statistical analysis is performed during a reconstruction process and computes a likelihood estimate that photons were coherently scattered from particular positions and angles of the object of interest (107) based on a computed probability density computed in accordance with said position and energy information of said detecting signals.

* * * * *